(12) United States Patent
Stein

(10) Patent No.: US 6,210,655 B1
(45) Date of Patent: Apr. 3, 2001

(54) SITE-SPECIFIC $^{13}$C-ENRICHED REAGENTS FOR DIAGNOSTIC MEDICINE BY MAGNETIC RESONANCE IMAGING

(75) Inventor: Stanley Stein, East Brunswick, NJ (US)

(73) Assignee: University of Medicine & Dentistry of NJ, Newark, NJ (US)

( * ) Notice: Subject to any disclaimer, the term of this patent is extended or adjusted under 35 U.S.C. 154(b) by 0 days.

(21) Appl. No.: 08/878,022

(22) Filed: Jun. 18, 1997

(51) Int. Cl.$^7$ .................................................. A61B 5/055
(52) U.S. Cl. ........................... 424/9.34; 424/9.3; 600/420
(58) Field of Search .......................... 424/9.4, 9.3, 1.69, 424/145.1, 158.1, 9.34, 9.341, 9.35, 9.36, 9.351, 1.81; 530/388.25, 389.3; 514/2; 436/173; 600/410, 420

(56) References Cited

U.S. PATENT DOCUMENTS 5,094,848 * 3/1992 Brixner ............................... 424/85.91
5,308,604 * 5/1994 Sinn et al. ........................... 424/1.53
5,593,658 * 1/1997 Bogdanov et al. .................. 424/9.34

\* cited by examiner

*Primary Examiner*—Michael G. Hartley
(74) *Attorney, Agent, or Firm*—Richard R. Muccino

(57) ABSTRACT

The present invention relates to site-specific $^{13}$C-enriched reagents for diagnostic medicine for magnetic resonance imaging. The site-specific $^{13}$C-enriched reagents may be represented by the formula: T-L-R. T is a site-specific targeting group which selectively binds to a disease-related target in an animal or human, R is an inert polymer containing repeating $^{13}$C reporting groups which provide a magnetic resonance imaging signal, and L is a linker group which connects the site-specific targeting group to the inert polymer. The site-specific $^{13}$C-enriched reagents are targeted to and capable of identifying, quantifying, and localizing disease-specific loci, such as blood clots, β-amyloid plaques of Alzheimer's disease, and tumors through the use of magnetic resonance imaging. The present invention also pertains to a method for employing the site-specific $^{13}$C-enriched reagents in a living mammal.

14 Claims, No Drawings

SITE-SPECIFIC $^{13}$C-ENRICHED REAGENTS FOR DIAGNOSTIC MEDICINE BY MAGNETIC RESONANCE IMAGING

BACKGROUND OF THE INVENTION

1. Field of the Invention

The present invention relates to site-specific $^{13}$C-enriched reagents for diagnostic medicine for magnetic resonance imaging. The site-specific $^{13}$C-enriched reagents may be represented by the formula: T-L-R. T is a site-specific targeting group which selectively binds to a disease-related target in an animal or human, R is an inert polymer containing repeating $^{13}$C reporting groups which provide a magnetic resonance imaging signal, and L is a linker group which connects the site-specific targeting group to the inert polymer. The site-specific $^{13}$C-enriched reagents are targeted to and capable of identifying, quantifying, and localizing disease-specific loci, such as blood clots, β-amyloid plaques of Alzheimer's disease, and tumors through the use of magnetic resonance imaging. The present invention also pertains to a method for employing the site-specific $^{13}$C-enriched reagents in a living mammal.

2. Description of the Background

Many diagnostic and therapeutic medical procedures for visualizing internal organs for the early detection and treatment of many diseases require the administration of contrast enhancing agents to improve the quality of the procedure. Contrast-enhancing agents are used in Magnetic Resonance Imaging (MRI), Computerized Tomography (CT), and X-ray procedures. Computerized Tomography provides a more sophisticated visualization of tissues and organs than does conventional X-ray techniques. Magnetic Resonance Imaging provides a superior soft tissue differentiation than does Computerized Tomography. Magnetic Resonance Imaging procedures generally employ the nuclear magnetic resonance of hydrogen ($^1$H) or fluorine ($^{19}$F). The nuclear magnetic resonance sensitivity of $^{19}$F is nearly equivalent to that of $^1$H but the biological background of $^{19}$F is negligible. The usefulness of a contrast enhancing agent depends upon the ease of the synthesis of the agent, the site-specificity of the agent, the resistance to in vivo hydrolysis of the agent, and a sufficient amount of signal from the agent along with a high signal-to-noise ratio.

In radioscintigraphy, a radioactive monoclonal antibody is typically injected into a patient for identifying and localizing a tumor, (reviewed in Bischof Delaloye, A. and Delaloye, B.: Tumor imaging with monoclonal antibodies. *Seminars in Nuclear Medicine* 25(2):144–164, 1995).

In radioimaging with monoclonal antibodies, a chemically modified (chelate) form of a monoclonal antibody is typically prepared and stored as a relatively stable product. To be used clinically, however, the monoclonal antibody sample must be mixed with a radioactive metal, such as $^{99m}$Tc, then purified to remove excess, unbound radioactive metal, and then administered to a patient within 6 hours, (Eckelman, W. C., Paik, C. H., and Steigman, J.: Three approaches to radiolabeling antibodies with $^{99m}$Tc. *Nuc. Med. Biol.* 16: 171–176, 1989). The entire process is cumbersome and dangerous due to the many manipulations requiring use and disposal of radioactivity. There is some health risk and fear accompanying injection of radioactivity into the patient.

Another example of imaging technology is the diagnosis of Alzheimer's disease, which afflicts over 3 million Americans and is increasing in incidence as the number of senior citizens increases. Currently, diagnosis is made by ruling out other causes for the symptoms of memory loss and dementia. The ability to diagnose Alzheimer's disease could also be critical to the development of an effective therapy. In particular, a therapeutic strategy that would arrest or reverse the buildup in the brain of β-amyloid plaques, which has been shown to be the cause of nerve cell loss, would require a means for imaging and measuring these deposits. The chemical, Congo red, has been shown to bind to β-amyloid plaques and a form of Congo red capable of chelating a radioactive metal has been prepared and proposed for use in imaging by radioscintigraphy (*Chem. & Eng. News*, Jun. 17, 1996, pages 33–34). Alternatively, the protein, tissue plasminogen activator, can be used in a radiolabeled form as a diagnostic reagent to image β-amyloid plaques, U.S. Pat. No. 5,589,154 (Anderson). Still another potential imaging agent is β-amyloid peptide, which can deposit into the plaque. Although β-amyloid plaques are within the brain, they are also present in the small and medium-sized arteries serving the brain, and are uniquely associated with Alzheimer's disease, (Vinters, H. V.; Cerebral amyloid angiopathy. A critical review. *Stroke* 18:311–324, 1987).

Another example of imaging technology is the diagnosis of blood clots. Despite the frequency of pulmonary thromboembolism and its associated morbidity and mortality, diagnosis remains suboptimal. Similarly, noninvasive detection of both deep vein and cerebral thrombosis is currently difficult. Various radiolabeled proteins, such as antifibrin monoclonal antibodies, (Rosebrough, S. F. and Hashmi, M.: Galactose-modified streptavidin-GC4 antifibrin monoclonal antibody conjugates: application for two-step thrombus/embolus imaging. *J. Pharm. Fxp. Ther.* 276(2): 770–775, 1996), fibrin-binding domain fragment of fibronectin (Rosenthall. L. and Leclerc, J.: A new thrombus imaging agent. Human recombinant fibrin binding domain labeled with In-ill. *Clin. Nucl. Med.* 20(5): 398–402, 1995), activated-platelet binding protein fragment (Muto, P., Lastoria, S., Varrella, P., et al.: Detecting deep venous thrombosis with technetium-$^{99m}$-labeled synthetic peptide P280. *J. Nucl. Med.* 36(8): 1384–1391, 1995) and (inactivated) tissue plasminogen activator (De Bruyn, V. H., Bergmann, S. R., Keyt, B. A. and Sobel, B. E.: Visualization of thrombi in pulmonary arteries with radiolabeled, enzymatically inactivated tissue-plasminogen activator. *Circulation* 92(5): 1320–1325, 1995) have been utilized for imaging thrombi.

The use of non-targeted, stable isotope-enriched contrast reagents, such as $^{13}$C glucose, has been described previously for imaging and for metabolic studies, (Shulman, R. G., Blamire, A. M., Rothman, D. L. and McCarthy, G. Nuclear magnetic imaging and spectroscopy of human brain function. *Proc. Natl. Acad. Sci. USA* 90(8): 3127–3133, 1993; Sonnewald, U., Gribbstad, I. S., Westergaard, N. Nilsen, G., Unsgard, G., Schousboe, A. and Peterson, S. B. Nuclear magnetic resonance spectroscopy: biochemical evaluation of brain function in vivo and in vitro. *Neurotox.* 15(3): 579–590, 1994). Also, the feature of targeted binding to a disease-indicating locus has been described for radioactive isotope-enriched reagents (see references above). Furthermore, tumor-localizing reagents containing metals such as gadolinium, which enhance contrast in proton ($^1$H) MRI, have been described, (Young, S. W., Qing, F., Harriman, A., Sessler, J. L., Dow, W. C., Mody, T. D., Hemmi, G. W., Hao, Y. and Miller, R. A. Gadolinium(III) texaphyrin: A tumor selective radiation enhancer that is detectable by MRI. *Proc. Natl. Acad. Sci. USA* 93: 6610–6615; Igarashi, N., Igarashi, S., Fujio, N. and Yoshida, A. Magnetic resonance imaging in the early diagnosis of cavernous sinus thrombosis. *Ophthalmologica* 209(5): 292–296, 1995; Williams, R. F., Siegle, R. L., Pierce, B. L. and Floyd, L. J. Analogs of synthetic melanin polymers for specific imaging applications. *Invest. Radiology* 29: S116–119, 1994; Orang-Khadivi, K., Pierce, B. L., Ollom, C. M., Floyd, L. J., Siegle, R. L. and Williams, R. F. New magnetic resonance imaging techniques for the detection of breast cancer. *Breast Cancer Res. Treat.* 32(1): 119–135, 1994.).

U.S. Pat. No. 4,624,846 (Goldenberg) discloses a method for enhancing the target specificity of antibody localization. The method comprises injecting a second antibody specific to a labeled target-specific antibody to reduce the level of non-targeted circulating specific antibody and thereby increase the localization ratio. Specifically, the method comprises injecting a human subject parenterally with a marker-specific antibody labeled with a pharmacologically inert radioisotope, capable of detection using a photoscanning device, or with a paramagnetic conjugate, capable of detection with a magnetic resonance detector, and subsequently scanning with the device or detector to detect and locate the site of uptake of the labeled antibody by the tumor. The improvement provided by the method comprises injecting the subject parenterally, at a time after injection of the marker-specific antibody sufficient to permit maximum selective uptake by the tumor, and prior to scanning, with a second, non-labeled antibody specific against the marker-specific antibody, in an amount sufficient to decrease the level of circulating labeled marker-specific antibody or fragment by 10–85% within 2–72 hours. Goldenberg discloses the use of numerous antibodies labeled with radionuclides for detection by photoscanning devices and paramagnetic species for detection by a magnetic resonance detector. The method is said to be useful to help determine the location of a tumor which produces or is associated with a cytoplasmic, intracellular, or cell-surface marker substance.

U.S. Pat. No. 5,236,694 (Antich et al. '694) discloses the use of $^{19}$F labelled compounds in methods of NMR imaging and spectroscopy. The compounds comprise a $^{19}$F-containing sensor moiety and a transport polymer, and may also comprise a spacer moiety to separate the sensor moiety and the transport polymer. Specifically, the method comprises administering to a living subject a $^{19}$F labelled NMR agent comprising (a) a transport polymer selected from the group consisting of dextran polymers and aminodextrans, having a molecular weight between approximately 100 d and 500 kd, and antibodies and fragments thereof, and (b) a $^{19}$F-containing sensor moiety selected from the group consisting of fluorinated alkyls, fluorinated acetates, fluoroaniline, and fluoroalkyl phosphonates, in an amount effective to provide a detectable NMR signal. The signal produced by the $^{19}$F labelled NMR agent in the subject is then detected.

U.S. Pat. No. 5,308,604 (Sinn et al.) discloses conjugates composed of a) at least one polyalcohol or a derivatized polyalcohol, b) at least one active agent, c) at least one linker, and d) a protein. The polyalcohols are compounds which are not recognized by the defense system of an organism as exogenous, such as sorbitol or derivatized sorbitol, with at least one OH group being replaced by $^{19}$F, $C^{19}F_3$, mono- or poly-$^{19}$F-substituted $C_1$–$C_4$ alkyl, mono-, di-, tri-, tetra- or penta-$^{19}$F-substituted phenyl. The active agent is a compound which is able to emit a signal to an external scanning device and/or is able to have a direct or indirect therapeutic effect on tumor tissue, and preferably is a $^{19}$F, $^{131}$I, or $^{132}$I labeled aromatic compound. The linker is a compound which may be used as a coupling member or spacing member between the protein and active agent. Examples of the linker, which are usually bifunctional, are 2,4-dichloropyrimidine, 4,4'-diisothiocyanoato-2,2'-stilbenedisulfoninc acid, and cyanuric chloride (2,4,6-trichloro-s-triazine). The protein is a compound which can be taken up by the tumor specifically or non-specifically, and is not recognized by the defense system of an organism as exogenous, such as autologous serum albumin. The conjugates are said to be suitable for providing a very sensitive method in nuclear medicine for the diagnosis of tumors and also offering methods for diagnosing tumors in X-ray diagnosis, computerized tomography, nuclear spin tomography, electron spin resonance spectroscopy, or electron microscopy.

U.S. Pat. No. 5,401,493 (Lohrmann et al.) discloses organic compounds for diagnostic imaging which contain at least one aryl group which has been derivatized to contain at least one perfluoro-1H,1H-neopentyl moiety. The perfluoro-1H,1H-neopentyl groups produce a single magnetic resonance to provide a maximum signal to noise ratio. A preferred perfluoro-1H,1H-neopentyl group is 3,5-$(CF_3)_3$C$(CH_2)$-$C_6H_3$-. A lipid emulsion may also be provided as a carrier vehicle to deliver the derivatized analog to a mammalian recipient.

U.S. Pat. No. 5,422,094 (Antich et al. '094) discloses an $^{19}$F labelled NMR composition said to be useful in methods of NMR imaging and spectroscopy comprising a $^{19}$F-containing sensor moiety and an antibody and optionally a spacer moiety to separate the sensor moiety and the antibody. The sensor moiety comprises —$COCF_3$ or —$NHCOCF_3$ and produces a single $^{19}$F NMR signal. The antibody reacts specifically with a particular antigen and is bound to the $^{19}$F-containing sensor moiety. Antich et al.'094 states that the spacer moiety can be used to isolate the $^{19}$F atoms from the substrate thereby enhancing the NMR signal produced. Antich et al.'094 states that the spacer moiety can be, for example, an alkyl hydrocarbon having a chain length of approximately 1–100 carbon atoms and containing an amino group, or alternatively, the spacer moiety can be selected from the group consisting of alkyl, alkoxy, aryl, and alkaryl hydrocarbons which contain an amino group, hydrazine, hydrazide, semicarbazide, and hydroxylamine. Antich et al.'094 state that the spacer moiety can optionally include one or more $^{19}$F atoms.

SUMMARY OF THE INVENTION

The present invention pertains to a site-specific $^{13}$C-enriched reagent for magnetic resonance imaging represented by the formula:

T-L-R wherein T is a site-specific targeting group which selectively binds to a disease-related target in an animal or human, R is an inert polymer containing repeating $^{13}$C reporting groups which provide a magnetic resonance imaging signal, and L is a linker group which connects the site-specific targeting group to the inert polymer.

The present invention also pertains to a method for employing a site-specific $^{13}$C-enriched reagent as a contrasting agent in magnetic resonance imaging to enhance the contrast of a targeted site in a living mammal which comprises the steps of:

(a) administering to a mammal an amount effective to produce a detectable magnetic resonance imaging signal of a site-specific $^{13}$C-enriched reagent for magnetic resonance imaging represented by the formula:

T-L-R wherein T is a site-specific targeting group which selectively binds to a disease-related target in an animal or human, R is an inert polymer containing repeating $^{13}$C reporting groups which provide a magnetic resonance imaging signal, and L is a linker group which connects the site-specific targeting group to the inert polymer; and (b) when the site-specific $^{13}$C-enriched reagent has reached the targeted site in the mammal, performing magnetic resonance imaging at that site to detect the signal produced by the site-specific $^{13}$C-enriched reagent.

DETAILED DESCRIPTION OF THE INVENTION

The present invention is directed to site-specific $^{13}$C-enriched reagents for diagnostic medicine by magnetic resonance imaging. Specifically, the invention relates to a magnetic resonance imaging reagent labeled with a stable isotope which may be represented by the formula:

T-L-R

T is a site-specific targeting group which selectively binds to a disease-related target in an animal or human, R is an inert polymer containing repeating $^{13}$C reporting groups which provide a magnetic resonance imaging signal, and L is a linker group which connects the site-specific targeting group to the inert polymer.

The site-specific $^{13}$C-enriched reagents of the present invention are targeted to and capable of binding selected loci in animals and humans, and thereby provide a means for detecting, identifying, localizing, and quantifying these loci by Magnetic Resonance Imaging. By employing the site-specific $^{13}$C-enriched reagents of the present invention, it is possible to diagnose the presence and status of particular diseases related to these loci. The $^{13}$C-enriched reagents are partly or fully enriched in $^{13}$C. Although the natural abundance of $^{13}$C is relatively high, these $^{13}$C-enriched reagents can be specifically probed to provide a signal in Magnetic Resonance Imaging when localized in vivo using techniques known to those skilled in the art, including detection of protons covalently bonded to $^{13}$C.

The site-specific targeting groups in the present invention are groups that preferentially bind to the site being targeted. The nature of the site-specific targeting group defines the diagnostic application of the particular version of the invention. The site-specific targeting group may be any organic compound, peptide, or protein, that can bind to a specific target or locus, i. e., act as a ligand and bind to a receptor. The site-specific targeting group may be a polyclonal antibody, monoclonal antibody, single chain antibody, or Fab fragment. The site-specific targeting group includes blood clot targeting groups, β-amyloid plaque targeting groups of Alzheimer's disease, Congo red, and tumor-specific antigen targeting groups. Proteins and peptides for use as targeting groups can be isolated from natural sources, prepared by recombinant DNA technology, or prepared by chemical synthesis. It is particularly advantageous to use antibodies of high specificity, e.g., affinity-purified antibodies and/or monoclonal antibodies.

In a preferred embodiment, the site-specific targeting group is employed to diagnose for Alzheimer's disease. The chemical, Congo red, has been shown to bind to β-amyloid plaques and a form of Congo red capable of chelating a radioactive metal has been prepared and used for imaging by radioscintigraphy. Alternatively, the protein, tissue plasminogen activator, can be used in a radiolabeled form as a diagnostic reagent to image β-amyloid plaques. Still another potential imaging agent is β-amyloid peptide, which can deposit into the plaque. Although β-amyloid plaques are within the brain, they are also present in the small and medium-sized arteries serving the brain, and are uniquely associated with Alzheimer's disease. Thus, it should be possible to administer the imaging agent intravenously, not requiring it to pass the blood brain barrier. In each case, imaging of the β-amyloid plaques would be done using stable isotope reagents.

In another preferred embodiment, the site-specific targeting group is employed to diagnose for blood clots. Despite the frequency of pulmonary thromboembolism and its associated morbidity and mortality, diagnosis remains suboptimal. Similarly, noninvasive detection of both deep vein and cerebral thrombosis is currently difficult. Various radiolabeled proteins, such as antifibrin 25 monoclonal antibodies, fibrin-binding domain fragment of fibronectin, activated-platelet binding protein fragment and (inactivated) tissue plasminogen activator have been utilized for imaging thrombi. As above, any of these targeting agents can be prepared in the $^{13}$C-enriched form.

The inert polymer of the present invention is an inert polymer group containing repeating $^{13}$C reporting groups which provide a magnetic resonance imaging signal. A preferred reporter group is $^{13}$C-labeled polyethylene glycol (PEG, also known as poly(ethylene oxide)), which can be prepared from $^{13}$C labeled ethylene oxide, which is commercially available from Isotech Inc. In addition to its role as a carrier of the reporter atoms for the magnetic resonance signal, use of polyethylene glycol as the conjugation partner is advantageous in the present invention for its pharmacological properties. These properties include providing an extended circulating half-life in blood, as well as preventing or minimizing attack by antibodies or proteases in blood (Davis, S., Abuchowski, A., Park, Y. K. and Davis, F. F. Alteration of the circulating half life and antigenic properties of bovine adenosine deaminase in mice by attachment of polyethylene glycol. *Clin. Exp. Immunol.* 46: 649–652, 1981). This description of polyethylene glycol does not rule out the use of other inert polymers, such as dextran, as the conjugation partner (Melton, R. G., Wiblin, C. N., Foster, R. L. and Sherwood, R. F. Covalent linkage of carboxypeptidase G2 to soluble dextrans-I. Properties of conjugates and effects on plasma resistance in mice. *Biochem. Pharmacol.* 36(1): 105–112, 1987). Furthermore, by localizing the signal generating element ($^{13}$C or $^1$H attached to $^{13}$C) to a repeating subunit, which is —(CH$_2$—CH$_2$—O—)n in polyethylene glycol, where n may range from 10 to 10,000 or more, the Magnetic Resonance Imaging instrument can be tuned to a specific and unique signal corresponding to the structure of polyethylene glycol. In this way, background signal from the natural abundance (ca. 1%) of $^{13}$C in other biomolecules, such as fatty acids, may be screened out. Even further, the multiple copies of the signal generating element appended to each locus-binding molecule (i.e. with respect to both the multiple copies of isotope atom per polymer chain and the opportunity to append several polymer chains to each binding molecule) serves as a means for signal amplification. Another advantage is that the inherent flexibility of the long, thin polyethylene glycol or other hydrophilic polymer chain should provide extensive molecular motion, resulting in a much stronger signal than possible by a peptide or protein bound to its corresponding receptor. A preferred reporter group is $^{13}$C-labeled polyethylene glycol, represented by the formula —(CH$_2$—CH$_2$—O—)n, where n may range from about 100 to about 100,000, preferably from about 1,000 to about 50,000, and more preferably from about 1,000 to about 10,000.

The linker group in the present invention is a group that connects the site-specific targeting group to the inert polymer. The linker group is employed as coupling member or spacer between the site-specific targeting group to the inert polymer. Linker groups are usually bifunctional compounds which use one functional group to enter into a chemical bond with the site-specific targeting group and use the second functional group to enter into a chemical bond with the inert polymer. Examples of linkers are m-maleimidobenzoyl-N-hydroxysuccinimide ester, for coupling a compound having a primary amino group with a compound having a thiol group, and ethylene glycobis (succinimidylsuccinate), for cross-linking two compounds having primary amino groups. Both of these cross-linkers, as well as a variety of other cross-linkers, are available from Pierce (Rockford, Ill.). The linker group is selectively attached to the site-specific targeting group at a site not directly involved in antigen-antibody or receptor-ligand binding, thereby allowing the site-specific targeting group to retain its binding function. Possible sites for attachment of the linker group to the site-specific targeting group include carbohydrate groups, amino groups, sulfhydryl groups, or combinations thereof.

The present invention extends to methods for preparing the site-specific $^{13}$C-enriched reagents. The site-specific $^{13}$C-enriched reagents may be synthesized using standard techniques and apparatus known to those skilled in the art. The ultimate site-specific $^{13}$C-enriched reagents are readily prepared using methods generally known in the chemical and biochemical arts.

In general, the site-specific $^{13}$C-enriched reagent can be synthesized by standard chemistry coupling reactions. $^{13}$C-Labeled polyethylene glycol can be or prepared from the $^{13}$C-labeled monomer, purified and activated, such as with but not limited to a protected thiol group (Woghiren, C., Sharma, B. and Stein, S. Protected thiol-polyethylene glycol: A new activated polymer for reversible protein modification. *Bioconj. Chem.* 4, 314–318, 1993). The activated, magnetic resonance responsive-enriched polyethylene glycol would then be reacted with the site-specific targeting group (protein, peptide or other organic molecule), using methods applicable to each particular product. For example, disulfide bond formation may be made by mixing the protected thiol-polyethylene glycol with a cysteine-containing protein or peptide. Otherwise, amino groups in the peptide or protein could be reacted at their primary amino groups (i.e. lysine side chains or the amino-terminus) using a heterobifunctional cross-linking agent with subsequent reaction to the thiol group of thiol-activated polyethylene glycol. Another approach would be to do a polymer extension reaction using a $^{13}$C enriched monomer on a pre-existing polymer, such as a monomethyl ether of polyethylene glycol of 2 kDa or a protected/activated polyethylene glycol of 2 kDa, as available from Shearwater Polymers Inc. (Huntsville, Ala.), and then proceed with the coupling to the site-specific targeting/binding molecule.

Also, a $^{13}$C-labeled copolymer having multiple attachment sites could be prepared (Nathan, A., Zalipsky, S., Ertel, S. I., Agathos, S. N., Yarmush, M. L. and Kohn, J. Copolymers of lysine and polyethylene glycol: A new family of functionalized drug carriers. *Bioconj. Chem.* 4, 54–62, 1993). In this way, multiple copies of the targeting/binding molecule, or a combination of different targeting and binding molecules can be linked to the same polymer molecule for achieving greater binding avidity or other special properties, such as enhanced cellular uptake after binding. Even further, the polyethylene glycol copolymer could be of especially high molecular weight for greatest signal generation, but designed to be unstable in vivo, so that it would eventually degrade into fragments small enough to be excreted. For example, individual 5,000-dalton subunits of $^{13}$C-labeled polyethylene glycol could be covalently linked to one another in a linear and/or branched manner through ester bonds to form a compound having an average molecular weight in the hundreds of thousands or millions of daltons. This macromolecular polyethylene glycol could be covalently linked to one or multiple copies of the site-specific targeting group.

The site-specific $^{13}$C-enriched reagents of the present invention may be used together with pharmaceutically acceptable carriers to provide pharmaceutical compositions which can be administered to mammals such as man in amounts effective to produce a detectable magnetic resonance imaging signal. The soluble carriers include lipid emulsions, liposomes, microparticles or microspheres. If the biological or pharmaceutical compound is water soluble a carrier is not required. Suitable carriers include propylene glycol-alcohol-water, isotonic water, sterile water for injection (USP), emulphor™-alcohol-water, cremophor-EL™ or other suitable carriers known to those skilled in the art. Other suitable carriers include isotonic water, sterile water for injection (USP), alone or in combination with other solubilizing agents such as ethanol, propylene glycol, or other conventional solubilizing agents known to those skilled in the art.

Of course, the type of carrier will vary depending upon the mode of administration desired for the pharmaceutical composition as is conventional in the art. A preferred carrier is an isotonic aqueous solution of the inventive compound.

The compounds of the present invention can be administered to mammals, e.g., animals or humans, in amounts effective to produce a detectable magnetic resonance imaging signal. Since the activity of the compounds and the degree of the desired diagnostic effect vary, the dosage level of the compound employed will also vary. The actual dosage administered will also be determined by such generally recognized factors as the body weight of the patient and the individual hyper sensitiveness of the particular patient.

The compounds of the present invention can be administered parenterally, in the form of sterile solutions or suspensions, such as intravenously, intramuscularly or subcutaneously in the carriers previously described.

For parental therapeutic administration, the compounds of the present invention may be incorporated into a sterile solution or suspension. These preparations should contain at least about 0.1% of the inventive compound, by weight, but this amount may be varied to between about 0.1% and about 50% of the inventive compound, by weight of the parental composition. The exact amount of the inventive compound present in such compositions is such that a suitable dosage level will be obtained.

The sterile solutions or suspensions may also include the following adjuvants: a sterile diluent, such as water for injection, saline solution, fixed oils, polyethylene glycol, glycerine, propylene glycol, or other synthetic solvent; antibacterial agents, such as benzyl alcohol or methyl paraben;

antioxidants, such as ascorbic acid or sodium metabisulfite; chelating agents, such as ethylenediaminetetraacetic acid (EDTA); buffers, such as acetates, citrates or phosphates; and agents for the adjustment of tonicity, such as sodium chloride or dextrose. The parental preparations may be enclosed in ampules, disposable syringes, or multiple dose vials made of glass or plastic.

It is especially advantageous to formulate the pharmaceutical compositions in dosage unit forms for ease of administration and uniformity of dosage. The term dosage unit forms as used herein refers to physically discrete units suitable for use as a unitary dosage, each unit containing a predetermined quantity of active ingredient calculated to produce the desired therapeutic effect in association with the pharmaceutical carrier.

In a specific embodiment, the invention is directed at a method for employing a site-specific $^{13}$C-enriched reagent as a contrasting agent in magnetic resonance imaging to enhance the contrast of a targeted site in a living mammal which comprises the steps of:

(a) administering to a mammal an amount effective to produce a detectable magnetic resonance imaging signal of a site-specific $^{13}$C-enriched reagent for magnetic resonance imaging represented by the formula:

T-L-R wherein T is a site-specific targeting group which selectively binds to a disease-related target in an animal or human, R is an inert polymer containing repeating $^{13}$C reporting groups which provide a magnetic resonance imaging signal, and L is a linker group which connects the site-specific targeting group to the inert polymer; and (b) when the site-specific $^{13}$C-enriched reagent has reached the targeted site in the mammal, performing magnetic resonance imaging at that site to detect the signal produced by the site-specific $^{13}$C-enriched reagent.

The present invention is further illustrated by the following examples which are not intended to limit the effective scope of the claims. All parts and percentages in the examples and throughout the specification and claims are by weight of the final composition unless otherwise specified.

EXAMPLES

Materials and Methods

1. Inactivated Tissue Plasminogen Activator-$^{13}$C-enriched polyethylene glycol conjugate.

Tissue plasminogen activator may be prepared from recombinant bacteria. After purification and renaturation, the protein would be inactivated with respect to its ability to activate plasminogen but not with respect to its ability to bind fibrin (De Bruyn, V. H., Bergmann, S. R., Keyt, B. A. and Sobel, B. E. Visualization of thrombi in pulmonary arteries with radiolabeled, enzymatically inactivated tissue-plasminogen activator. *Circulation* 92(5): 1320–1325, 1995). The inactivated tissue plasminogen activator could be reacted with a bifunctional cross-linking reagent, such as sulfosuccinimidyl(4-iodoacetyl)aminobenzoate. After removal of excess cross-linking reagent, the protein derivative could then be reacted with a thiol-activated form of $^{13}$C-enriched polyethylene glycol. The conjugate would then be purified, formulated and administered to the patient, in a manner known to those skilled in the art. This reagent could then provide a means of detecting blood clots and β-amyloid plaques of Alzheimer's disease by Magnetic Resonance Imaging.

2. β-amyloid Peptide-$^{13}$C-enriched Polyethylene Glycol Conjugate.

The amyloid-forming peptide of Alzheimer's disease is derived by enzymatic cleavage of the carboxy-terminal portion of the amyloid precursor protein (Sisodia, S. S. and Price, D. L. Role of the β-amyloid protein in Alzheimer's disease. *FASEB J*. 9:368–370, 1995). The amyloid plaques increase in size by further deposition of β-amyloid peptide and exogenous β-amyloid peptide would deposit into pre-existing plaques (Esler et al., A β-deposition Inhibition Screen Using Synthetic Amyloid. Nature Biotechnology 15:258–263 (1997). β-amyloid peptide would be chemically synthesized with an additional residue of cysteine at its amino-terminus. After purification, the desired conjugate could be prepared by mixing the peptide with a thiopyridine protected form of $^{13}$C-enriched thiol-polyethylene glycol (see reference by Woghiren et al., above).

3. Fibrin-binding Peptide-$^{13}$C-enriched polyethylene glycol conjugate.

For the detection of thrombi, it is possible to use a synthetic peptide corresponding in sequence to the fibrin-binding domain fragment of fibronectin, as previously described using a radiolabeled fibrin-binding peptide (see reference by Rosenthall and Leclerc, above). Fibrin-binding peptide would be chemically synthesized with an additional residue of cysteine at its amino- or carboxy-terminus. After purification, the desired conjugate could be prepared by mixing the peptide with a thiopyridine protected form of $^{13}$C-enriched thiol-polyethylene glycol.

4. Antifibrin Monoclonal Antibody-$^{13}$C-enriched polyethylene glycol conjugate.

Monoclonal antibodies may be reacted with activated $^{13}$C polyethylene glycol, in a manner so as not to interfere with the binding properties of the antibody. Such conjugates of antibodies to fibrin may be used to image thrombi, such as with the GC4 antibody described above (see reference by Rosebrough and Hashmi, above).

Throughout this application, various publications have been referenced. The disclosures in these publications are incorporated herein by reference in order to more fully describe the state of the art.

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

What is claimed is:

1. A site-specific $^{13}$C-enriched reagent for magnetic resonance imaging represented by the formula:

T-L-R wherein T is a site-specific targeting group which selectively binds to a disease-related target in an animal or human, R is an inert polymer containing repeating $^{13}$C reporting groups which provide a magnetic resonance imaging signal, wherein the inert polymer is $^{13}$C-labeled polyethylene glycol, and L is a linker group which connects the site-specific targeting group to the inert polymer.

2. The magnetic resonance imaging reagent according to claim 1, wherein the site-specific targeting group is an organic compound, peptide, or protein selected from the group consisting of polyclonal antibodies, monoclonal antibodies, single chain antibodies, and Fab fragments.

3. The magnetic resonance imaging reagent according to claim 2, wherein the site-specific targeting group is selected from the group consisting of blood clot targeting groups, β-amyloid plaque targeting groups of Alzheimer's disease, Congo red, and tumor-specific antigen targeting groups.

4. The magnetic resonance imaging reagent according to claim 2, wherein the site-specific targeting group is selected from the group consisting of antifibrin monoclonal antibodies, fibrin-binding domain fragment of fibronectin, activated-platelet binding protein fragment, and inactivated tissue plasminogen activator.

5. The magnetic resonance imaging reagent according to claim 3, wherein the site-specific targeting group is Congo red.

6. The magnetic resonance imaging reagent according to claim 4, wherein the site-specific targeting group is inactivated tissue plasminogen activator.

7. The magnetic resonance imaging reagent according to claim 3, wherein the site-specific targeting group is a β-amyloid peptide of Alzheimer's disease.

8. A method for employing a site-specific $^{13}$C-enriched reagent as a contrasting agent in magnetic resonance imaging to enhance the contrast of a targeted site in a living mammal which comprises the steps of:

(a) administering to a mammal an amount effective to produce a detectable magnetic resonance imaging signal of a site-specific $^{13}$C-enriched reagent for magnetic resonance imaging represented by the formula:

T-L-R wherein T is a site-specific targeting group which selectively binds to a disease-related target in an animal or human, R is an inert polymer containing repeating $^{13}$C reporting groups which provide a magnetic resonance imaging signal, wherein the inert polymer is $^{13}$C-labeled polyethylene glycol, and L is a linker group which connects the site-specific targeting group to the inert polymer; and (b) when the site-specific $^{13}$C-enriched reagent has reached the targeted site in the mammal, performing magnetic resonance imaging at that site to detect the signal produced by the site-specific $^{13}$C-enriched reagent.

9. The method according to claim 8, wherein the site-specific targeting group is an organic compound, peptide, or protein selected from the group consisting of polyclonal antibodies, monoclonal antibodies, single chain antibodies, and Fab fragments.

10. The method according to claim 9, wherein the site-specific targeting group is selected from the group consisting of blood clot targeting groups, β-amyloid plaque targeting groups of Alzheimer's disease, Congo red, and tumor-specific antigen targeting groups.

11. The method according to claim 9, wherein the site-specific targeting group is selected from the group consisting of antifibrin monoclonal antibodies, fibrin-binding domain fragment of fibronectin, activated-platelet binding protein fragment, and inactivated tissue plasminogen activator.

12. The method according to claim 10, wherein the site-specific targeting group is Congo red.

13. The method according to claim 11, wherein the site-specific targeting group is inactivated tissue plasminogen activator.

14. The method according to claim 10, wherein the site-specific targeting group is a β-amyloid peptide of Alzheimer's disease.

* * * * *

UNITED STATES PATENT AND TRADEMARK OFFICE
Certificate

Patent No. 6,210,655 B1                                                                 Patented: April 3, 2001

On petition requesting issuance of a certificate for correction of inventorship pursuant to 35 U.S.C. 256, it has been found that the above identified patent, through error and without any deceptive intent, improperly sets forth the inventorship.
   Accordingly, it is hereby certified that the correct inventorship of this patent is: Stanley Stein, East Brunswick, NJ (US); and Gaetano T. Montelione, Highland Park, NJ (US).

Signed and Sealed this Seventeenth Day of July 2007.

<div align="right">

WILLIAM R. DIXON, JR.
*Special Program Examiner*
Technology Center 1600

</div>